United States Patent
Benetti

(10) Patent No.: US 6,769,429 B1
(45) Date of Patent: Aug. 3, 2004

(54) NASAL DILATION DEVICE

(76) Inventor: Giulio Benetti, 9177 Currey Rd., Dixon, CA (US) 95620

( * ) Notice: Subject to any disclaimer, the term of this patent is extended or adjusted under 35 U.S.C. 154(b) by 70 days.

(21) Appl. No.: 10/124,041

(22) Filed: Apr. 16, 2002

(51) Int. Cl.[7] ................................................ A62B 9/00
(52) U.S. Cl. ................................ 128/200.24; 606/199
(58) Field of Search ..................... 128/200.24; 606/191, 606/198, 199, 201, 204.45; 604/104

(56) References Cited

U.S. PATENT DOCUMENTS

| 5,533,499 | A |   | 7/1996  | Johnson |              |
|-----------|---|---|---------|---------|--------------|
| 5,533,503 | A |   | 7/1996  | Doubek et al. |        |
| D379,513  | S | * | 5/1997  | Ierulli ................... D24/135 |
| 5,961,537 | A | * | 10/1999 | Gould ................... 606/204.45 |
| 6,098,616 | A | * | 8/2000  | Lundy et al. ........... 128/200.24 |
| 6,375,667 | B1 | * | 4/2002 | Ruch ....................... 606/199 |
| 6,453,901 | B1 | * | 9/2002 | Ierulli ................... 128/200.24 |

FOREIGN PATENT DOCUMENTS

EP       0 778 014 A1  *  11/1997   ............ 128/200.24

* cited by examiner

Primary Examiner—Glenn K. Dawson
(74) Attorney, Agent, or Firm—Thomas R. Lampe

(57) ABSTRACT

A nasal dilation device includes a single, integral strip of flexible resilient material having a central portion for positioning over and in engagement with the top of an individual nose and opposed end portions including independently flexible upper and lower finger elements diverging from one another. Adhesive tape elements overly the end portions for releasably securing the end portion to opposed sides of the individual's nose.

6 Claims, 1 Drawing Sheet

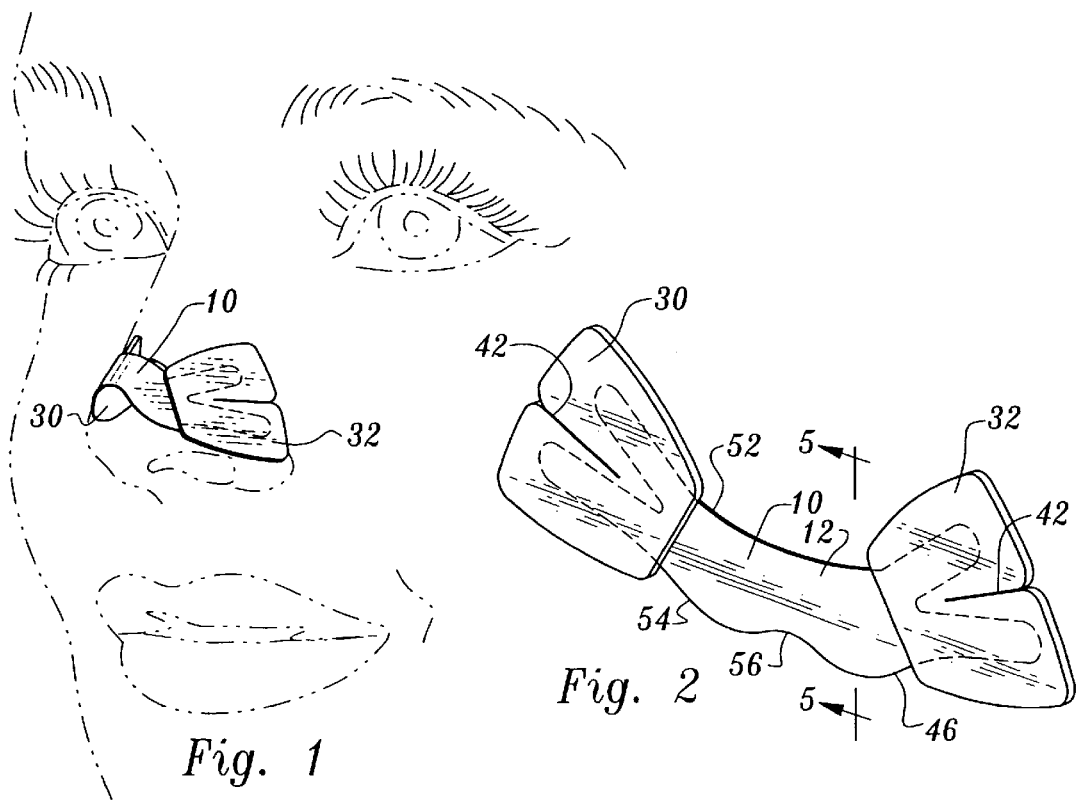
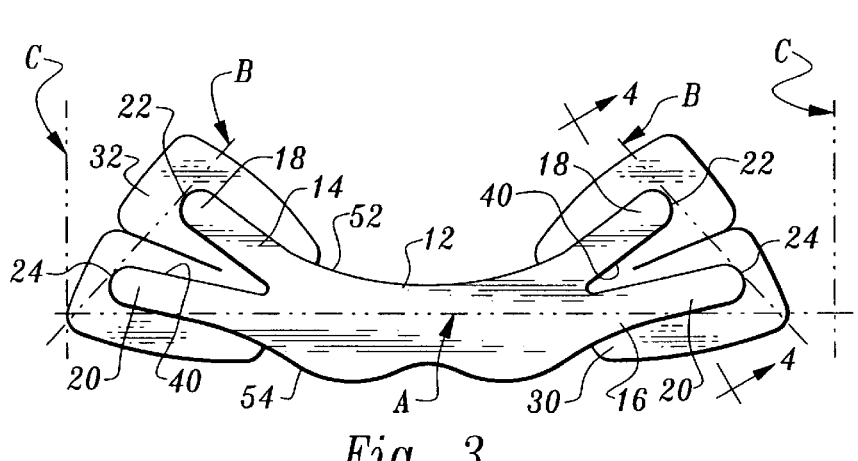
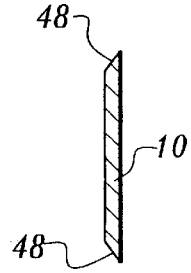
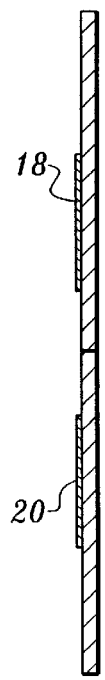

NASAL DILATION DEVICE

TECHNICAL FIELD

This invention relates to a device for resisting inward movement of outer wall tissue of nasal passages of a nose during breathing.

BACKGROUND OF THE INVENTION

Nasal dilators that resist inward movement of the outer wall tissue of the nasal passages during breathing are known. U.S. Pat. Nos. 5,533,499, issued Jul. 9, 1966, and 5,533,503, issued Jul. 9, 1996, disclose nasal dilators comprising truss-members. The truss-member includes a flexible strip of material having a first end region, a second end region and an intermediate segment. The first and second end regions are adapted to engage the outer wall tissue of first and second nasal passages of the nose. The intermediate segment is configured to traverse a portion of the nose located between the first and second nasal passages. The truss-member further includes first and second resilient bands secured to the strip of material adjacent opposite edges of the intermediate segment. The resiliency of the first and second bands purportedly acts to stabilize the outer wall tissue and thereby prevent the outer wall tissue of the first and second nasal passages from drawing in during breathing.

DISCLOSURE OF INVENTION

The present invention also relates to a nasal dilation device utilized to resist inward movement of outer wall tissue of the nasal passages of a nose during breathing.

The nasal dilation device of the present invention is characterized by its relative simplicity, enabling the dilator to be of relatively low cost construction, as well as provide a high degree of comfort to the user when applied to the nose.

The nasal dilation device of the present invention includes a single, integral strip of flexible, resilient material having a substantially uniform thickness and a normally planar state and being disposed along a linear longitudinal axis.

The strip of flexible, resilient material includes a central portion for positioning over the top of an individual's nose and opposed end portions affixed to the central portion for positioning at opposite sides of the individual's nose.

Each end portion comprises independently flexible upper and lower finger elements diverging from one another and from said linear longitudinal axis. The upper and lower finger elements have free distal finger element ends.

The free distal finger element ends terminate at a first imaginary line defining an angle with a second imaginary line orthogonal to said longitudinal axis. The angle falls within the range of from about 35 degrees to about 45 degrees. The upper finger elements of the end portions are shorter than the lower finger elements.

The nasal dilation device also includes adhesive tape elements overlying the end portions for releasably securing the end portions to the opposite sides of the individual's nose to maintain the strip of flexible, resilient material in flexed and bent condition and to continuously apply pulling forces at the opposite sides of the individual's nose to maintain the nasal passageways thereof opened.

Other features, advantages and objects of the present invention will become apparent with reference to the following description and accompanying drawings.

BRIEF DESCRIPTION OF DRAWINGS

FIG. 1 is a perspective view showing a preferred embodiment of a nasal dilation device constructed in accordance with the teachings of the present invention positioned on an individual's nose;

FIG. 2 is an enlarged, frontal, perspective view of the nasal dilation device in flat condition;

FIG. 3 is a rear, elevational view of the flat nasal dilation device;

FIG. 4 is an enlarged, cross-sectional view of the nasal dilation device taken along line 4—4 in FIG. 3; and FIG. 5 is a greatly enlarged, partial sectional view taken along the line 5—5 of FIG. 2.

BEST MODE FOR CARRYING OUT THE INVENTION

Referring now to the drawings, a nasal dilation device constructed in accordance with the teachings of the present invention includes a single, integral strip 10 of flexible, resilient material having a substantially uniform thickness and a normally planar state shown in FIGS. 2—5. The flexible, resilient material is preferably a clear plastic material, for example a transparent polymeric material. The thickness of the strip suitably in the range of from about 0.2 mm to about 0.6 mm.

The strip is disposed along a linear longitudinal axis A (see FIG. 3).

Strip 10 includes a central portion 12 for positioning over and in engagement with the top of an individual's nose, as shown in FIG. 1. The strip additionally includes opposed end portions 14, 16 affixed to the central portion for positioning at opposite sides of the individual's nose.

Each end portion comprises independently flexible finger elements, an upper finger element 18 and a lower finger element 20. These upper and lower finger elements diverge from one another and from the linear longitudinal axis A. The upper and lower finger elements respectively have free distal finger element ends 22, 24.

These free distal finger element ends at each end portion terminate at a first imaginary line B defining an angle with a second imaginary line C orthogonal to the linear longitudinal axis A. FIG. 3 illustrates the first and second imaginary lines B and C. The angle falls within the range of from about 35 degrees to about 45 degrees. The upper finger elements 18 of the end portions are shorter than the lower finger elements thereof.

Adhesive tape elements 30, 32 are adhesively secured to and overly the end portions 14, 16 for releasably securing the end portions to the opposite sides of the individual's nose, as shown in FIG. 1. This maintains the strip of flexible, resilient material in flexed and bent condition and opposed pulling forces are thus exerted by the nasal dilation device at opposite sides of the nose to maintain the passageways thereof open. If desired, the adhesive tape elements can be formed of transparent or semi-transparent material. Also, if desired, adhesive may be applied to the back surfaces of finger elements 18 and 20.

The upper and lower finger elements 18, 20 of each of the end portions 14, 16 define an opening 40. The edges of the upper and lower finger elements at the openings 40 form a generally V-shaped configuration. The adhesive tape elements 30, 32 extend across the openings 40 defined by the upper and lower finger elements and beyond the outer edges of the upper and lower finger elements. The adhesive tape elements of course only have an adhesive coating at the backside or skin engagement side thereof.

The adhesive tape elements define slits 42 communicating with the openings 40. This allows flexing of the finger elements to be unimpeded by the adhesive tape elements so that the finger elements and the adhesive tape elements can more readily conform to the shape of the wearer's nose. This adds to the comfort of the wearer.

Further adding to the wearer's comfort and contributing to function of the device is the angled orientation of the distal finger element ends 22, 24 as described above. The fact that the upper finger elements of the end portions are shorter than the lower finger elements thereof allows the device to be worn comfortably without the upper finger elements engaging the user's face at locations other than the nose itself. The lower finger elements and lower segments of the adhesive tape elements effectively distribute forces applied to the lower, larger portions of the nose that they cover.

Another comfort feature is the fact that the free distal finger element ends of the upper and lower finger elements are rounded and that the adhesive tape elements have rounded corners also, the adhesive tape elements being spaced from the free distal finger element ends.

Yet one more comfort feature employed in the device is the fact that the outer peripheral edge 46 of the strip is chamfered, as designated by reference numeral 48 in FIG. 5. This provides for a higher degree of flexibility of the strip than would otherwise be the case.

The peripheral edge of the strip includes an upper strip edge 52 and a lower strip edge 54. Lower strip edge 54 forms a concavity 56 where the central portion 12 is positioned on the top of the individual's nose. The lower strip edge is convex on both sides of the concavity. The concavity is for receiving the top of the individual's nose to facilitate and maintain proper placement of the nasal dilation device on the individual's nose.

The invention claimed is:

1. A nasal dilation device comprising, in combination:
    a single, integral strip of flexible, resilient material having a substantially uniform thickness and a normally planar state and being disposed along a linear longitudinal axis, said strip of flexible, resilient material including a central portion for positioning over the top of an individual's nose and opposed end portions affixed to said central portion for positioning at opposite sides of the individual's nose, each end portion comprising independently flexible upper and lower finger elements diverging from one another and from said linear longitudinal axis having free distal finger element ends, said free distal finger element ends terminating at a first imaginary line defining an angle with a second imaginary line orthogonal to said linear longitudinal axis falling within the range of from about 35 degrees to about 45 degrees, said upper finger elements of said end portions being shorter than the lower finger elements thereof; and
    adhesive tape elements overlying said end portions for releasably securing said end portions to the opposite sides of the individual's nose to maintain said strip of flexible, resilient material in flexed and bent condition and to continuously apply opposed pulling forces at the opposite sides of the individual's nose to maintain the nasal passageways thereof open, the upper and lower finger elements of each of said end portions defining an opening, said adhesive tape elements extending across the openings defined by the upper and lower finger elements and beyond outer edges of said upper and lower finger elements, said upper and lower finger elements both diverging upwardly from said linear longitudinal axis and the free distal finger element ends of both said upper and lower finger elements along with the portions of said adhesive tape element covering said free distal finger element ends being located above said linear longitudinal axis.

2. The nasal dilation device according to claim 1 wherein said adhesive tape elements define slits communicating with said openings.

3. The nasal dilation device according to claim 1 wherein said flexible, resilient material is transparent plastic material.

4. The nasal dilation device according to claim 1 wherein said substantially uniform thickness is in the range of from about 0.2 mm to about 0.6 mm.

5. A nasal dilation device comprising, in combination:
    a single, integral strip of flexible, resilient material having a substantially uniform thickness and a normally planar state and being disposed along a linear longitudinal axis, said strip of flexible, resilient material including a central portion for positioning over the top of an individual's nose and opposed end portions affixed to said central portion for positioning at opposite sides of the individual's nose, each end portion comprising independently flexible upper and lower finger elements diverging from one another and from said linear longitudinal axis having free distal finger element ends, said free distal finger element ends terminating at a first imaginary line defining an angle with a second imaginary line orthogonal to said linear longitudinal axis falling within the range of from about 35 degrees to about 45 degrees, said upper finger elements of said end portions being shorter than the lower finger elements thereof; and
    adhesive tape elements overlying said end portions for releasably securing said end portions to the opposite sides of the individual's nose to maintain said strip of flexible, resilient material in flexed and bent condition and to continuously apply opposed pulling forces at the opposite sides of the individual's nose to maintain the nasal passageways thereof open, said strip of flexible, resilient material having an upper strip edge and a lower strip edge, said lower strip edge forming a concavity where said central portion is positioned over the top of the individual's nose and being convex on both sides of said concavity, said concavity for receiving the top of the individual's nose to facilitate and maintain proper placement of the nasal dilation device on the individual's nose.

6. A nasal dilation device comprising, in combination:
    a single, integral strip of flexible, resilient material having a substantially uniform thickness and a normally planar state and being disposed along a linear longitudinal axis, said strip of flexible, resilient material including a central portion for positioning over the top of an individual's nose and opposed end portions affixed to said central portion for positioning at opposite sides of the individual's nose, each end portion comprising independently flexible upper and lower finger elements diverging from one another and from said linear longitudinal axis having free distal finger element ends, said free distal finger element ends terminating at a first imaginary line defining an angle with a second imagi nary line orthogonal to said linear longitudinal axis falling within the range of from about 35 degrees to about 45 degrees, said upper finger elements of said end portions being shorter than the lower finger elements thereof; and adhesive tape elements overlying said end portions for releasably securing said end portions to the opposite sides of the individual's nose to maintain said strip of flexible, resilient material in flexed and bent condition and to continuously apply opposed pulling forces at the opposite sides of the individual's nose to maintain the nasal passageways thereof open, said strip of flexible, resilient material having an outer peripheral edge, said outer peripheral edge being chamfered.

* * * * *